(12) United States Patent
Weber et al.

(10) Patent No.: US 10,111,577 B2
(45) Date of Patent: Oct. 30, 2018

(54) ENDOSCOPIC INSTRUMENT WITH AN LED ILLUMINATION MODULE

(75) Inventors: Bernd Claus Weber, Karlsruhe (DE); Rudolf Heimberger, Oberderdingen (DE); Klaus Schrumpf, Kraichtal-Münzesheim (DE); Adrian Mahlkow, Berlin (DE)

(73) Assignee: Richard Wolf GmbH, Knittlingen (DE)

( * ) Notice: Subject to any disclaimer, the term of this patent is extended or adjusted under 35 U.S.C. 154(b) by 1157 days.

(21) Appl. No.: 12/906,269

(22) Filed: Oct. 18, 2010

(65) Prior Publication Data

US 2011/0092772 A1 Apr. 21, 2011

(30) Foreign Application Priority Data

Oct. 19, 2009 (DE) .................. 10 2009 049 683

(51) Int. Cl.
*A61B 1/00* (2006.01)
*A61B 1/06* (2006.01)
*A61B 1/12* (2006.01)
*G02B 23/24* (2006.01)

(52) U.S. Cl.
CPC ........ *A61B 1/0008* (2013.01); *A61B 1/00114* (2013.01); *A61B 1/0607* (2013.01); *A61B 1/0676* (2013.01); *A61B 1/0684* (2013.01); *A61B 1/12* (2013.01); *A61B 1/128* (2013.01); *G02B 23/2461* (2013.01); *A61B 1/0638* (2013.01)

(58) Field of Classification Search
CPC ... A61B 1/00096; A61B 1/128; A61B 1/0684; G02B 23/2461; F21V 19/003; F21V 19/005
See application file for complete search history.

(56) References Cited

U.S. PATENT DOCUMENTS

| 4,301,790 | A | 11/1981 | Bol et al. |
| 5,721,463 | A | 2/1998 | Snyder |
| 6,492,725 | B1* | 12/2002 | Loh et al. ............ 257/723 |
| 2006/0063976 | A1* | 3/2006 | Aizenfeld ........ A61B 1/00096 600/179 |

(Continued)

FOREIGN PATENT DOCUMENTS

| DE | 28 35 331 A1 | 2/1980 |
| DE | 696 28 901 T2 | 4/2004 |

(Continued)

OTHER PUBLICATIONS

Machine translation of JP 2003-024276.*

(Continued)

*Primary Examiner* — Alexandra L Newton
(74) *Attorney, Agent, or Firm* — Panitch Schwarze Belisario & Nadel LLP

(57) ABSTRACT

An endoscopic instrument is provided with an LED illumination module having at least one LED arranged at the distal end of the instrument and having an electrical connection lead attached to this LED. The connection lead is a coaxial cable, which extends from the distal end to the proximal end of the instrument, and is designed for leading away the waste heat produced by the LED. At least one electrical conductor of the coaxial cable is connected to the LED in a heat-conducting manner.

16 Claims, 13 Drawing Sheets

(56) References Cited

U.S. PATENT DOCUMENTS

| | | | |
|---|---|---|---|
| 2007/0191684 A1* | 8/2007 | Hirata | 600/179 |
| 2008/0128740 A1* | 6/2008 | Yamashita et al. | 257/99 |
| 2008/0183043 A1 | 7/2008 | Spinnler et al. | |

FOREIGN PATENT DOCUMENTS

| | | |
|---|---|---|
| DE | 10 2007 015 492 A1 | 7/2008 |
| EP | 1 911 389 A1 | 4/2008 |
| JP | H01-222579 A | 9/1989 |
| JP | H04-344716 A | 12/1992 |
| JP | H08-228161 A | 9/1996 |
| JP | H10-92279 A | 4/1998 |
| JP | 11216113 A | 8/1999 |
| JP | 2003-024276 A | 1/2003 |
| JP | 2006-202664 A | 8/2006 |
| JP | 2007-142249 A | 6/2007 |
| JP | 2008-300884 A | 12/2008 |
| WO | 0233312 A2 | 4/2002 |
| WO | 2007018098 A1 | 2/2007 |

OTHER PUBLICATIONS

Office Action dated Jul. 5, 2010 in German Appln. Ser. No. 10 2009 049 683.1.
EP Search Report dated Mar. 21, 2011 in EP Application No. 10013248.9.
Office Action dated Mar. 4, 2014 in JP Application No. 2010-234757.
Office Action dated Mar. 15, 2016 in JP Application No. 2010234757.

\* cited by examiner

ENDOSCOPIC INSTRUMENT WITH AN LED ILLUMINATION MODULE

BACKGROUND OF THE INVENTION

The invention relates to an endoscopic instrument having an LED illumination module.

With endoscopes, it may be advantageous to arrange an illumination device in the form of an LED directly in the region of the distal end of the endoscope, since one may thus make do without fiber-optics in the inside of the endoscope. However, with the use of LEDs at the distal end of the endoscope, the problem of leading away the waste heat produced by the LED arises. This is necessary in order, for example, to avoid burns of the surrounding tissue. It is known, for example, from Japanese patent application publication (Kokai) JP 11-216113 A to cool the LED with the help of supplied air.

An illumination device for an endoscope is known from European patent application publication EP 1 911 389 A1, with which the waste heat produced by the LED is led away via connection electrodes of the LED. However, these connection electrodes are very large in cross section, and are rigid, so that an application in a flexible endoscope is only possible with limitations.

BRIEF SUMMARY OF THE INVENTION

It is the object of the invention to provide an endoscopic instrument having an LED illumination module, which permits a flexible design of the endoscope shaft and simultaneously a targeted removal of the heat produced by the LED.

This object is achieved by an endoscopic instrument having at least one LED illumination module, comprising at least one LED arranged at the distal end of the instrument and having an electrical connection lead attached to this LED, wherein the connection lead is a coaxial cable which extends from the distal end to the proximal end of the instrument and is designed for leading away the waste heat produced by the LED, and wherein at least one electrical conductor of the coaxial cable is connected to the LED in a heat-conducting manner. Preferred embodiments are set forth in the claims, subsequent description and the attached Figs.

The endoscopic instrument according to the invention comprises at least one LED illumination module. This is designed such that the at least one LED serving for illumination is arranged in the region of the distal end of the instrument. In this manner, one may make do without the usually applied fiber optics in the endoscope shank. Fiber-optic bundles are sensitive and very often have optical losses. These disadvantages too are avoided by the arrangement of an LED at the distal end of the instrument.

The illumination module comprises at least one LED, but instead one may also apply several LEDs, for example in order to achieve a greater illumination intensity. The at least one LED has, in the known manner, an electrical connection lead, via which the LED is supplied with energy. The electrical connection lead in a medical instrument or endoscope would then run from the LED to the proximal end of the instrument, and be connected to an electricity source there or even outside the instrument.

According to the invention, one envisages also using the electrical connection lead for leading away the waste heat produced by the LED. This means that one uses the heat-conducting properties of the electrical connection lead, in particular its metallic conductors, in order to lead away waste heat. For this, at least one of the electrical conductors in the connection lead is dimensioned such that it permits an adequate heat conduction, in particular has an adequately high thermal conductance, in order to lead away from the LED a significant part, preferably most, of the waste heat occurring at the LED. Preferably, materials with a high thermal conductivity, as for example silver or copper or an alloy having a significantly high share of such materials, are used as electrical conductors. Moreover, together with the thermal conductivity, one must furthermore optimize the cross-sectional area of the conductor, in order to realize an adequate heat transfer, in particular an adequately large absolute thermal conductance of the electrical conductor or conductors. A smaller cross section may be sufficient with a larger thermal conductivity. A larger material cross section is necessary with a smaller specific thermal conductivity. Since the electrical connection lead usually extends in the opposite direction to the radiating direction of the light, one may thus lead away the arising heat from the illuminated region via the electrical connection lead. Thus with the endoscopic instrument, the heat is led away in the direction of the proximal end of the instrument, and thus the region of the object to be observed, i.e., the region surrounding the distal region of the instrument, for example the surrounding tissue, is ideally kept largely free of the waste heat produced by the LED.

The conductor is connected to the LED in a thermally conductive manner, for example soldered to it, in order to ensure an optimized heat transfer from the LED onto the at least one conductor of the electrical connection lead, wherein ideally a connecting region or heat transition region is created, which is as large-surfaced as possible.

According to the invention, the connection lead is designed as a coaxial cable or as a lead having a construction similar to the coaxial cable, and at least one of the electrical conductors of the coaxial cable is directly or indirectly connected to the LED in a thermally conductive manner. Thereby, a cable having at least one inner electrical conductor and at least one outer electrical conductor surrounding this, or a cable having a comparable construction, is to be understood as a coaxial cable, wherein the conductors do not necessarily need to be arranged concentrically to one another.

With a sufficient flexibility of the cable, which is important for bendable systems as are applied in bendable endoscopes, one may provide a large cross-sectional area of the electrical conductor or conductors, which may be used for leading away the heat, due to the use of a coaxial cable or a comparable cable arrangement. In a coaxial cable, one may achieve maximal cross-sectional areas for the conductors which may be used for heat removal, with a simultaneously minimized outer diameter. Here, a maximally large cross-sectional area and thus a maximal possible heat transfer may be achieved with as small as possible an outer periphery.

As specified, the coaxial cable is preferably designed in a flexible manner, so that it may be inserted in the shank of a flexible endoscope, and the bending ability of the endoscope shank is not compromised. For this, further preferably, at least one of the conductors of the coaxial cable may be composed of several individual conductors, in particular wires. Such a conductor may in particular be composed of a multitude of strands. These, as is known from conventional coaxial cables, may be braided with one another or may be simply arranged in the cable in a bundled manner extending in the longitudinal direction of the cable, and in particular the outer conductor may be designed as a wire braiding. The use of a multitude of strands ensures a large flexibility of the cable.

Preferably, several or even all electrical conductors of the connection lead are used for leading away the waste heat produced by the LED. For this, preferably several or all electrical conductors of the connection lead are connected in a thermally conductive manner to the LED, for example soldered. Thereby, as large-surfaced as possible heat transfer regions to the LED are created ideally for all of these conductors, so that the heat transfer of the LED onto the conductors is optimized.

Further preferably, the at least one electrical conductor of the connection lead, which is used for heat removal, has a greater cross-sectional area, preferably at least three times greater, further preferably at least five times greater cross-sectional area, than is necessary for the electrical power transmission to the LED. A sufficient heat removal is ensured by this cross-sectional area which is enlarged with respect to the cross-sectional area required for the electric power transmission. Thus, a large part of the waste heat produced by the LED may be led away via this electrical conductor. Further preferably, several or all electrical conductors of the connection lead have a cross-sectional area which is enlarged in such a manner.

The at least one electrical conductor of the connection cable is preferably connected to the LED in a heat-conducting manner with a maximally large cross-sectional area. An optimal heat transfer from the LED to the conductor is ensured in this manner.

The at least one electrical conductor of the connection lead may be thermally conductively connected to the LED in a direct manner but also indirectly via connection elements, e.g. a connection plate. Thus it is possible for the one LED or, optionally several LEDs, to be arranged for example on a circuit board or a highly thermally conductive copper element, and for the electrical conductor or conductors to be connected in an electrically conductive manner to the circuit board or the strip conductors incorporated on the circuit board or to the highly thermally conductive copper element. For example, the LEDs may be bonded on a copper ring which is directly connected to the shield or to the outer conductor of the coaxial cable. A circuit board is preferably designed such that it has a small thermal resistance, i.e. for its part, preferably has a high thermal conductivity and a low thickness/height. For example, for this purpose, one may also dimension strip conductors formed on or in the circuit board, in such a large manner in cross section, that a heat removal is possible via these strip conductors onto the conductor of the connection cable. An optimal heat transfer is created by a direct connection of the light diode to the at least one conductor of the connection cable. The electrical connection contacts of the light diode may have a smaller cross section than the cross section of the conductor of the connection lead. Further regions of the LED which do not serve for the electrical connection, may be brought into heat-conducting contact with the conductor of the connection lead, for example via a heat-conducive medium, such as thermally conductive paste or likewise, in order, despite this, to create an optimized heat transfer from the light diode onto the whole cross-sectional area of the conductor of the connection lead. This thermally conductive medium may thereby be designed in an electrical insulating manner.

The electrical connection lead is preferably connected in a heat-conducting manner to the at least one LED at a rearward surface. The rearward surface of the LED is thereby a surface which is away from the radiating direction for the light produced by the LED. With an arrangement in an endoscopic instrument, this is preferably the rearward surface of the LED, the surface facing the proximal end of the instrument.

Particularly preferably, at least the outer electrical conductor of the connection lead, which is designed as a coaxial cable or as a comparable cable, is connected to the LED in a thermally conductive manner. Thereby, the heat flow via the peripheral surface of the connection lead along the endoscope shank, to the outer surroundings, is optimized. However, it is also possible for the outer as well as the inner electrical conductor of the coaxial cable to be connected in a thermally conductive manner to the LED, in order to serve the removal of heat.

The outer conductor of the coaxial cable may have a greater thickness in the radial direction than an insulation layer which is situated between an inner and the outer electrical conductor of the coaxial cable, in order to maximize the cross-sectional area of the thermally conductive conductor. This means that the outer electrical conductor of the coaxial cable, with this embodiment, preferably has a larger cross-sectional area than is usual with known coaxial cables. Ideally, only a very thin insulation layer, which may only just ensure the electrical insulation, is provided between the inner and the outer conductor. In this manner, the material share of the cable having a poor thermal conductivity is minimized in its cross-sectional area, whereas the thermally conductive parts, specifically the electrical conductors, may be designed as large as possible in cross section. Simultaneously, the outer diameter of the coaxial cable may be kept as small as possible, which is advantageous with regard to the restricted spatial conditions in the shank of an endoscopic instrument.

It may be preferable for the inner conductor of the coaxial cable to have a minimized cross-sectional area, which in its size is adapted to the electrical power to be transmitted, in order to further minimize the cross-sectional area of the insulation layer. This means that with this embodiment, the cross-sectional area of the inner electrical conductor is preferably selected only as large as is necessary for the electrical power to be transmitted to the LED. Thus, this cross-sectional area and the peripheral length in the cross section, are kept as small as possible, whereby also the peripheral extension of the required insulation layer and thus its cross-sectional area is minimized. Instead of this, with this embodiment, preferably the cross-sectional area of the outer conductor is designed sufficiently large in order to be able to accomplish the necessary leading away of heat from the LED.

According to a further preferred embodiment, one may make do without an electrical insulation on the outer periphery of the outer conductor of the coaxial cable. An electrical insulation with this design is only provided between the two concentric conductors of the coaxial cable which serve for the electrical energy supply of the LED. A further improvement of the ratio of the share of the cross section of the connection lead which has good thermal conductivity to the share with a poor thermal conductivity is achieved by this.

An electrical short circuit between the two concentric conductors is ruled out by the insulation between the electrical conductors. A short-circuit via external elements of the endoscopic instrument is ruled out due to the concentric arrangement. In this manner, one may thus optimally utilize the complete cross section of the coaxial cable for energy transmission and for leading heat.

The illumination module may be integrated into the endoscopic instrument in a fixed manner. Here, the illumination module may be provided as a pre-manufactured module, which is then integrated into the instrument. Moreover, it is also possible to arrange the illumination module in the endoscopic instrument in a removable or exchangeable manner so that, for example if damaged, it may be easily exchanged or may be removed for cleaning and disinfection. Moreover, it is also possible to provide different illumination modules for different application purposes, which may be exchanged in the instrument or instead may also be integrated into this in a fixed manner. The electrical connection lead extends from the LED, arranged at the distal end of the endoscopic instrument, to the proximal end, and thus ensures the electrical energy supply from an electricity source to the distal end of the instrument and to the LED arranged there. Moreover, as described above, it also serves for the removal of waste heat or dissipation of heat from the LED. This heat is led away from the connection lead at least in part to the proximal end of the instrument. Thereby, optionally, at least a part of the waste heat of the LED may be led away from the connection lead to a cooling body which is situated at a distance from the LED, to which cooling body the electrical connection lead or at least one conductor of the electrical connection lead is likewise connected in a heat-conducting manner. The waste heat may then be radiated to the outside, for example to the surrounding air, via this cooling body. With regard to this cooling body, in the simplest embodiment it may be the surface of the endoscope hand-grip or of an interface to the surroundings, which is otherwise present in any case. Moreover, a certain heat dissipation also takes place via the outer peripheral surface of the electrical connection lead, in particular in the form of a coaxial cable, so that the waste heat of the LED may thus be released to the surroundings over the whole length of the illumination module or its connection lead. In this manner, the maximal temperature, which occurs in a localized manner, is also reduced on the (endoscope) surface, since the dissipated heat energy as a whole is distributed over a larger surface. Damage or burns to the tissue may be avoided in this manner.

The connection lead in the endoscopic instrument is preferably designed as a continuous lead from the distal to the proximal end, for optimizing the heat removal. Thus, connection locations which have a worse heat transfer are thus avoided, and as a whole the thermal conductivity over the complete length from the distal to the proximal end of the instrument is optimized.

Further preferably, the LED is surrounded peripherally and/or on the front side by elements which have a lower thermal conductivity than the electrical connection lead. These elements may, for example, be designed in the form of a thermal insulation layer, for example of plastic. By this, it is ensured that most of the waste heat is led away via the electric connection lead and is not led away to the regions directly surrounding the LED, in particular on the front side of the LED. Temperature peaks, which could lead to burns, are avoided in the region of the distal end of the endoscopic instrument in this manner. These elements having a lower thermal conductivity, i.e. thermally insulating elements, may directly surround the LED as a part of the illumination module, or instead also be designed surrounding the illumination module, for example in the endoscopic instrument. Thus, for example, even the wall of the tip or of the head of the endoscopic instrument may be designed of plastic and thus in a thermally insulating manner.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
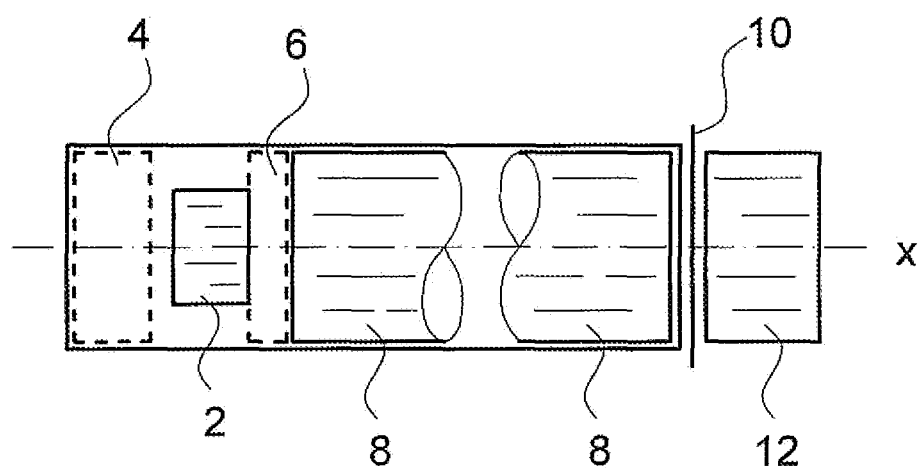
FIG. 1 is a longitudinally truncated, schematic view of an embodiment of an LED illumination module according to the invention.

As is schematically shown in FIG. 1, an illumination module according to the invention comprises an LED unit 2, which is arranged in the region of the distal end. The LED unit may contain one or several LEDs. On the distal end of the LED unit 2, this is protected by a protective glass unit 4 in the example shown here. This protective glass unit 4, which does not necessarily need to be a part of the LED illumination module and is therefore represented in a dashed manner, but which may also be assigned to the distal end of the endoscope, may also be designed as a lens or as a lens unit. This protective glass unit 4 closes the illumination module to the outside and protects the LED unit 2, lying proximally therebehind, from contamination and damage. Moreover, the protective glass unit 4 may act in a thermally insulating manner, so that waste heat emitted by the LED unit does not get to the distal end of the LED illumination module or the endoscope, or gets there only to a limited extent. As shown here by example, but not obligatory, a thin connection plate 6 is arranged proximally of the LED unit 2, via which connection plate the LED unit 2 is connected in an electrically conductive manner to a connection lead 8 which forms a connection unit. This connection plate may be designed as a circuit board or, for example, also as a metallic platelet, copper platelet or similar. The arrangement of the LED unit 2 on the connection plate 6 is designed such that not only an electrical contacting, but also a highly thermally conductive connection, between the LED unit 2 and the connection plate 6 and/or the connection lead 8 is created. If the LED unit is not in direct thermally conductive contact with the connection lead 8, furthermore, apart from the electrical contacting between the connection lead 8 and the connection plate 6, a highly thermally conductive connection between the connection plate 6 and the connection led 8 is provided. The highly thermally conductive connection between the LED unit 2 and the connection plate 6, or between the LED unit 2 and the connection lead 8, and/or between the connection plate 6 and the connection lead 8, may be produced either by direct contact or via a heat-conducting connection which may be produced, for example, by soldering, welding or bonding, or instead by a highly thermally conductive medium, such as a thermally conductive paste or a thermally conductive adhesive.

An interface 10 is provided at the proximal end of the connection lead 8 and may be arranged, for example, at the proximal end of an endoscope shank. This interface 10, on the one hand, serves for the electrical contacting of the connection lead 8 and, on the other hand, also for the thermal contacting. For example, this interface 10 may in turn create the connection to a circuit board 12 which serves for the electrical connection.

According to the invention, one envisages the waste heat produced by the LED unit 2 being transmitted via the connection plate 6 or directly to the connection lead 8, and being led proximally by this, and already a significant part of this waste heat being dissipated via the periphery of the connection lead 8 to the endoscope shank and from there to the surroundings. The residual share of the waste heat, which is still present at the proximal end of the connection lead 8 as the case may be, is dissipated via the proximal-side interface 10 to further elements leading away the heat or to the surroundings. Thus, with a preferably simultaneous thermal insulation of the LED unit in the lateral and distal direction (there for example via the protective glass unit 4), one may thus succeed in waste heat produced by the LED unit 2 at least not being completely directly dissipated to the environment of the LED unit, but being led away from this in a targeted manner in the proximal direction via the connection lead 8. For this, in particular the electrical conductors of the connection lead 8, which are designed of metal, are dimensioned in their cross section, such that they have a sufficient coefficient of thermal conductivity, in order to lead away the occurring waste heat completely or at least to a large extent. In this respect, excessive heating and, as the case may be, injuries which this entails, for example of surrounding tissue in the environment of the LED unit 2, are avoided.

Figure 2:
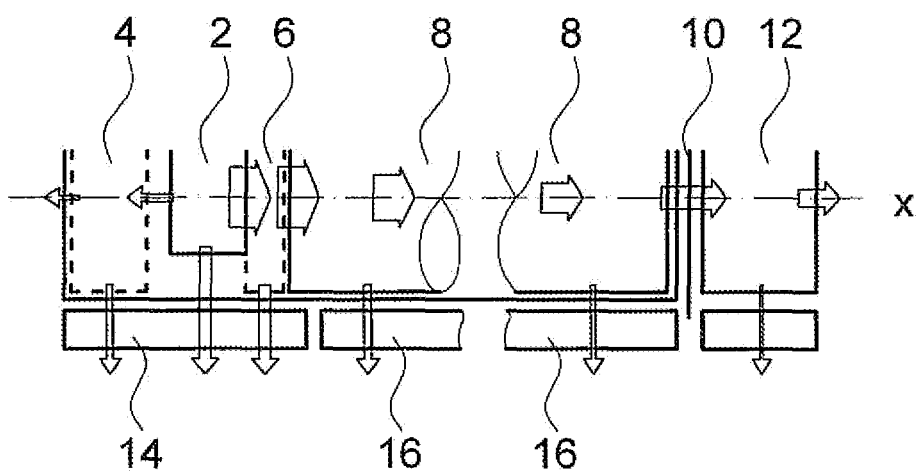
FIG. 2 is a longitudinally truncated, schematic view of the integration of an LED illumination module according to FIG. 1 into an endoscope.

FIG. 2 now schematically shows the integration of the LED illumination module according to FIG. 1 into an endoscope. As recognizable there, for example, the LED unit 2, the optional connection plate 6 and the protective glass unit 4, which covers the LED unit 2 on the distal end and which, depending on the embodiment, may be assigned to the LED illumination module or the distal end of the endoscope and therefore is represented dashed in FIG. 2, are arranged in an endoscope head 14. This endoscope head may, for example, be designed in a rigid manner, whereas an endoscope shank 16, connecting proximally in the direction of the longitudinal axis X, may, for example, be designed in a flexible manner. However, the endoscope head 14 and the endoscope shank 16 may also be designed in a rigid or completely flexible manner. The connection lead 8 extends through the endoscope shank 16 to the proximal end of the endoscope, on which the interface 10 for the electrical contacting of a proximal-end circuit board 12 is arranged. The interface 10 does not necessarily serve for contacting the circuit board 12. Here, for example, one may also provide a connection plug or the like for the electrical contracting. Optionally, the connection lead 8 may instead extend beyond the endoscope to an external apparatus.

The heat flow in the endoscope, which is achieved according to the invention, is represented schematically by the arrows represented in FIG. 2. As is represented by the thin arrows, only a small part of the heat is led away from the LED unit 2 into the direct environment, i.e. via the wall of the endoscope head 14, endoscope shank 16, and the protective glass unit 4. The largest part of the heat, as is represented by the wider arrows, is transmitted in the proximal direction in a highly thermally conductive connection to the connection plate 6, and from this is transmitted in turn via a highly thermally conductive connection to the connection lead 8, or, if one makes do for example without the optional connection plate 6, directly from the LED unit 2 to the connection lead 8. The heat from the connection lead 8 is led further proximally, wherein the connection lead 8, depending on the construction of the endoscope, dissipates a part of the heat or even the complete heat in the lateral direction, whereby the heat quantity to be transmitted further proximally reduces with increasing distance from the distal end of the endoscope. Thus, only a part of the waste heat transmitted from the LED unit 2 to the connection lead 8, optionally no heat whatsoever, is led away from the connection lead 8 proximally via the interface 10. A further part of the heat, which is led away, is dissipated to the surroundings via the connection lead 8 in the course of its extension in the longitudinal direction X. According to the invention, in this example, one succeeds in the waste heat produced by the LED unit 2 not being directly emitted to the direct surroundings, but being released in the proximal direction and there being released via the connection lead 8 to the surroundings via a large surface, whereby localized temperature peaks, which could lead to burns for example of the surrounding tissue, are avoided.

Figure 3:
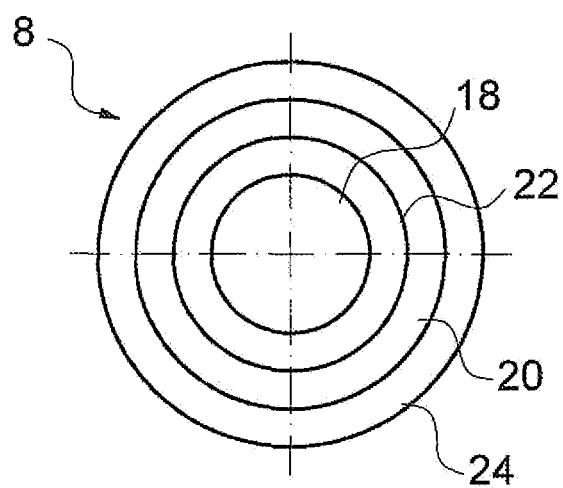
FIG. 3 is a schematic, cross-sectional view of a connection lead according to a first embodiment of the invention.
Figure 4:
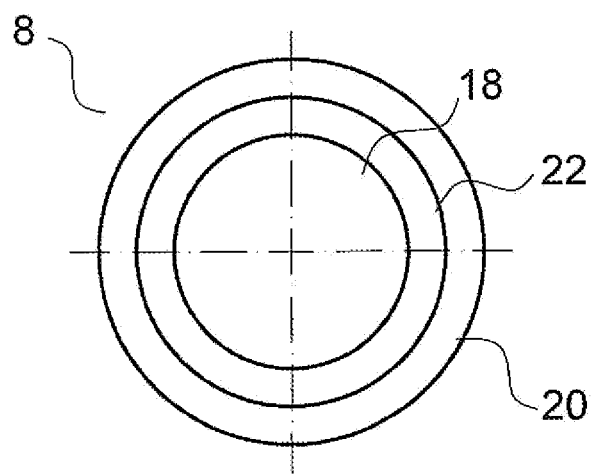
FIG. 4 is a schematic, cross-sectional view of a connection lead according to a second embodiment of the invention.
Figure 5:
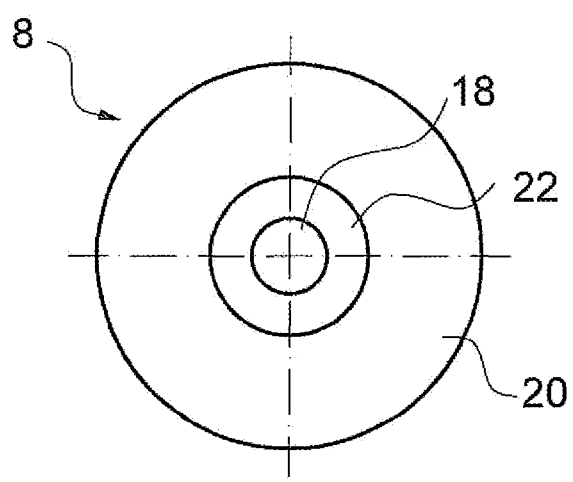
FIG. 5 is a schematic, cross-sectional view of a connection lead according to a third embodiment of the invention.

The connection lead 8 according to the invention is designed as a coaxial cable or in an arrangement which is comparable to the coaxial cable. Examples of this are shown in FIGS. 3 to 5. FIG. 3 shows a first embodiment of such a coaxial cable having an inner conductor 18 and an outer, annular conductor 20 concentrically surrounding the inner conductor 18. The inner conductor 18 and the outer conductor 20 are electrically insulated from one another by an annular insulation layer 22. Additionally, in the embodiment according to FIG. 3, an outer insulation layer 24 is provided, which peripherally surrounds the outer conductor 20. According to the invention, one envisages the inner conductor 18 as well as the outer conductor 20 serving for the electrical connection of the LED unit 2. The conductors 18 and 20 simultaneously serve for leading away heat in the proximal direction, as explained by FIGS. 1 and 2. For this, at least one of the conductors has a cross-sectional area which is larger, preferably more than three or five times larger than that cross sectional area which would be necessary for the transmission of the necessary electrical energy to the LED unit 2. In this manner, a significantly larger absolute thermal conductance is achieved, than would be applied with conventional electrical connection leads as would be necessary for the connection of the applied LED unit.

It is desirable to optimize the cross-sectional area of the electrical conductors 18 and 20 in order to increase the thermal conductance of the connection lead 8 or its electrical conductors 18 and 20. For this, a further embodiment is shown schematically in FIG. 4. With this example, one makes do without the outer insulation layer 24. This, with the same total diameter of the connection lead 8, permits the enlargement of the cross-sectional areas of the electrical conductors 18 and 20 in comparison to the embodiment in FIG. 3, by the diameter of the inner conductor 8 being able to be enlarged and/or the radial thickness of the outer conductor 20 being able to be enlarged.

A further optimization of the cross section of the electrical conductors 18 and 20 is recognizable in the embodiment according to FIG. 5. There, one likewise makes do without the outer insulation layer 24 (see FIG. 3). Moreover, the inner conductor 18 is instead minimized in its diameter. Ideally, the inner conductor 18 thereby has only such a diameter or such a cross-sectional area which is necessary for transmitting the required electrical power or the occurring electrical current. This leads to an inner conductor 18 which is relatively small in diameter, whereby the peripheral length of the required insulation layer 22, which surrounds the inner conductor 18 at the outer periphery, is reduced in size. The total cross-sectional area of the insulation layer 22 is reduced in size by this, and the outer conductor 20 may be designed in a particularly thick manner in the radial direction, so that as a whole, the cross-sectional area of the electrical conductors 18 and 20 together may be maximized given a constant outer diameter. In principle, in order to ensure a high flexibility of the connection lead 8, the conductor 20 may consist of several layers which may be displaced relative to one another in the longitudinal direction. The thermal conductivity is also improved with the larger cross-sectional area of the metallic conductors 18 and 20, which is to say that the absolute coefficient of thermal conductivity increases, whereby one may achieve an improved leading away of the heat from the LED unit 2.

The arrangement of the previously described LED illumination module or of several LED illumination modules in an endoscope is now described hereinafter by example and by the FIGS. 6 to 10. For this, the FIGS. 6 to 7 schematically show distal plan views and perspective views of an endoscope shank.

Figure 6A:
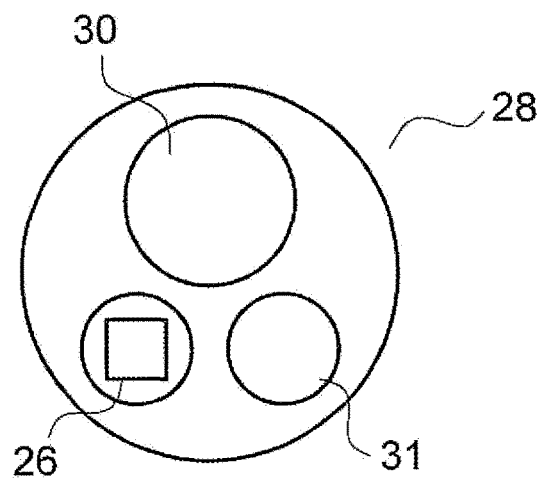
FIG. 6*a* is a distal-end plan view of a first example of the arrangement of an LED illumination module in an endoscope.
Figure 6B:
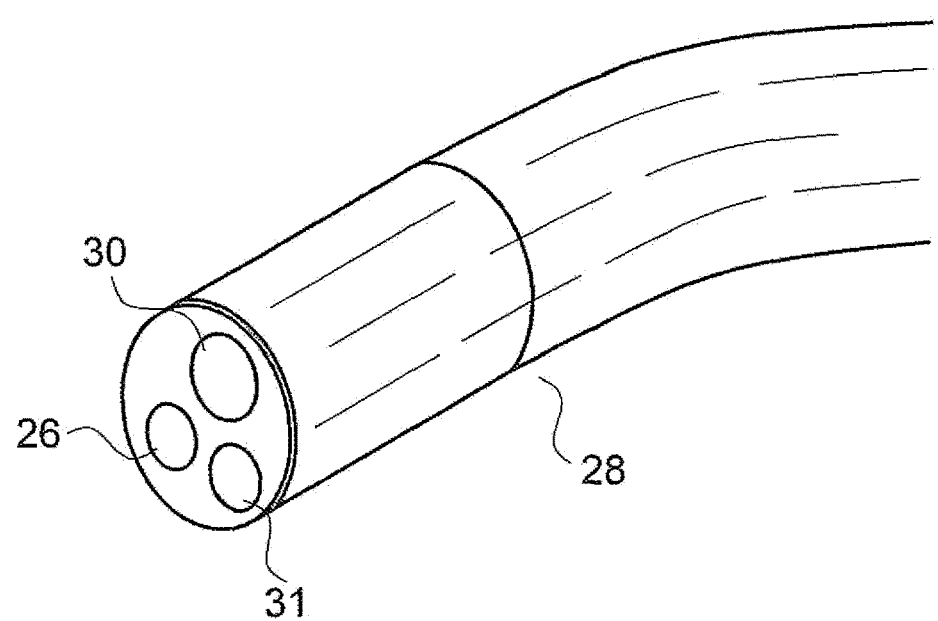
FIG. 6*b* is a perspective view of the arrangement according to FIG. 6*a*.

With the embodiment according to FIGS. 6a and 6b, an LED illumination module 26 is provided in the endoscope shank and may be preferably designed in the previously described manner. Since the endoscope shank 28 with this embodiment is designed in a comparatively thin manner, in a flexible manner for example, only one LED is provided in the LED illumination module 26. Moreover, one instrument channel 30 and a picture sensor unit 31 are further arranged in the endoscope shank 28.

Figure 7A:
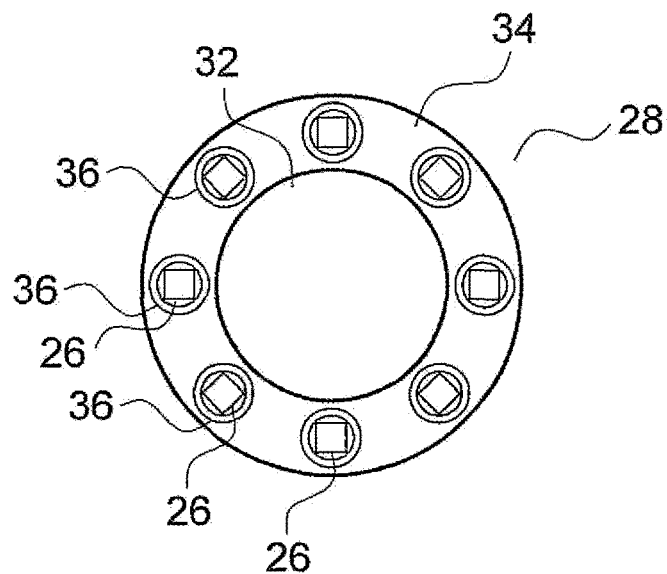
FIG. 7*a* is a distal-end plan view of a second example of the arrangement of LED illumination modules in an endoscope.
Figure 7B:
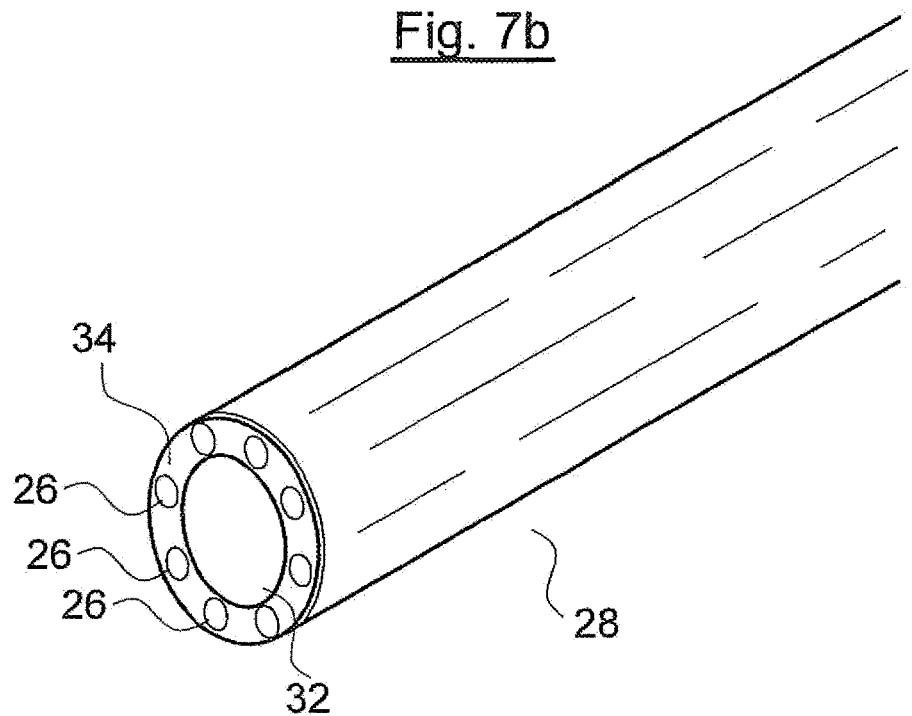
FIG. 7*b* is a perspective view of the arrangement according to FIG. 7*a*.

With the embodiment according to FIGS. 7a and 7b, several, here eight, LED illumination modules 26 are provided, which are arranged in an annular manner around a central channel. Here too, the illumination modules 26 may be designed in the previously described manner. Thereby, the several individual LED illumination modules 26 in each case have their own connection lead 8 which extends proximally. Alternatively, several LED illumination modules 26 may be connected to a common connection lead 8, which also serves for leading away the heat, for example via a circuit board. In order to keep the heat flow density in the radial direction from the LED illumination modules 26 to the shank tube 34 as small as possible, the individual illumination modules 26 are surrounded in each case by a thin plastic flexible tube 36 or a flexible tube of another material having a comparatively low thermal conductivity, whereby a reduction of the heat flow in the lateral direction is achieved. This is particularly advantageous, for example since with this embodiment the LED illumination modules 26 are arranged very close to the surrounding shank tube 34, which with a rigid endoscope is further formed of metal. Insofar as this is concerned, an excessive heat transfer onto the shank tube 34 may be prevented by the flexible tubes 36 of a material having a comparatively low thermal conductivity, and as described above, the heat may be led away proximally via the connection leads 8, and be continuously dissipated to the surroundings over a large length/large peripheral surface of the shank tube 34.

Figure 8:
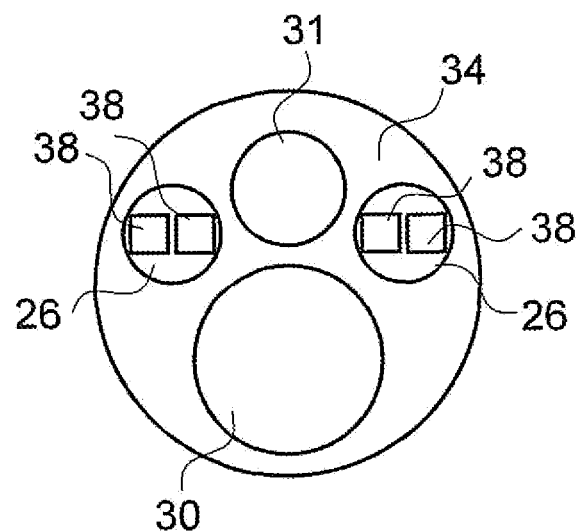
FIG. 8 is a distal-end plan view of a third example of the arrangement of LED illumination modules in an endoscope.
Figure 9:
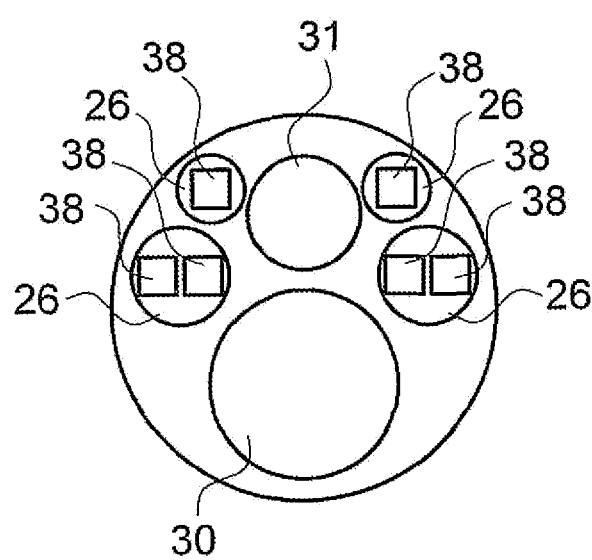
FIG. 9 is a distal-end plan view of a fourth example of the arrangement of LED illumination modules in an endoscope.

With the embodiment according to FIG. 8, two illumination units 26 are arranged laterally of a picture sensor unit 31, in the shank 34 or the endoscope head. The LED illumination modules 26, in the example shown here, in each case have two LEDs 38. Additionally, an instrument channel 30 is further provided in the shank 34 or in the endoscope head. With the embodiment according to FIG. 9, four LED illumination modules 26 are provided, two having in each case two LEDs 38 and two having in each case one LED 38, which are arranged peripherally of a picture sensor unit 31. With the several LED illumination modules 26, these may be for example LED illumination modules 26 which emit different wavelengths. These, for example two, LED illumination modes 26, for example those which have only one LED 38, are designed for emitting white light, and the two other LED illumination modules 26 are designed for emitting violet excitation light for fluorescence endoscopy.

Figure 10:
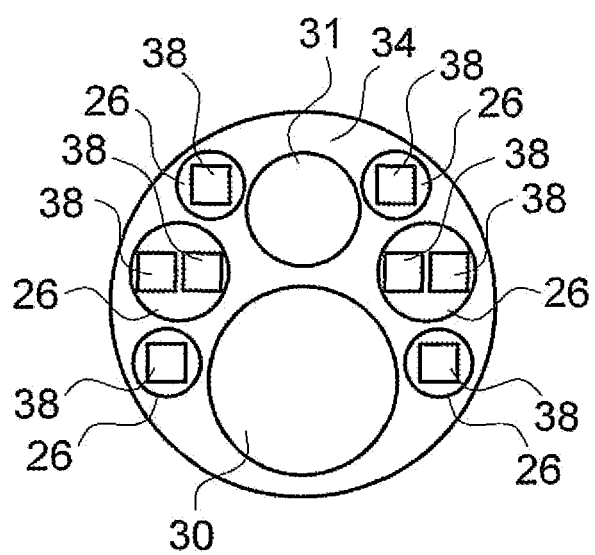
FIG. 10 is a distal-end plan view of a fifth example of the arrangement of LED illumination modules in an endoscope.

FIG. 10 shows an arrangement of in total six LED illumination modules 26 in a shank tube 34. Here too, the different LED illumination modules may be designed for emitting light of different wavelengths. Here too, the picture sensor unit 31 and the instrument channel 30 are provided in the previously described manner. It is clear with this example how the available space may be utilized in an optimal manner, thus how, using the modular concept, the provided light quantity and/or the functionality may be optimized without an enlargement of the total diameter of the endoscope, by the availability and the application of illumination modules of different sizes and, optionally, with different functions (e.g. different emission regions).

Figure 11:
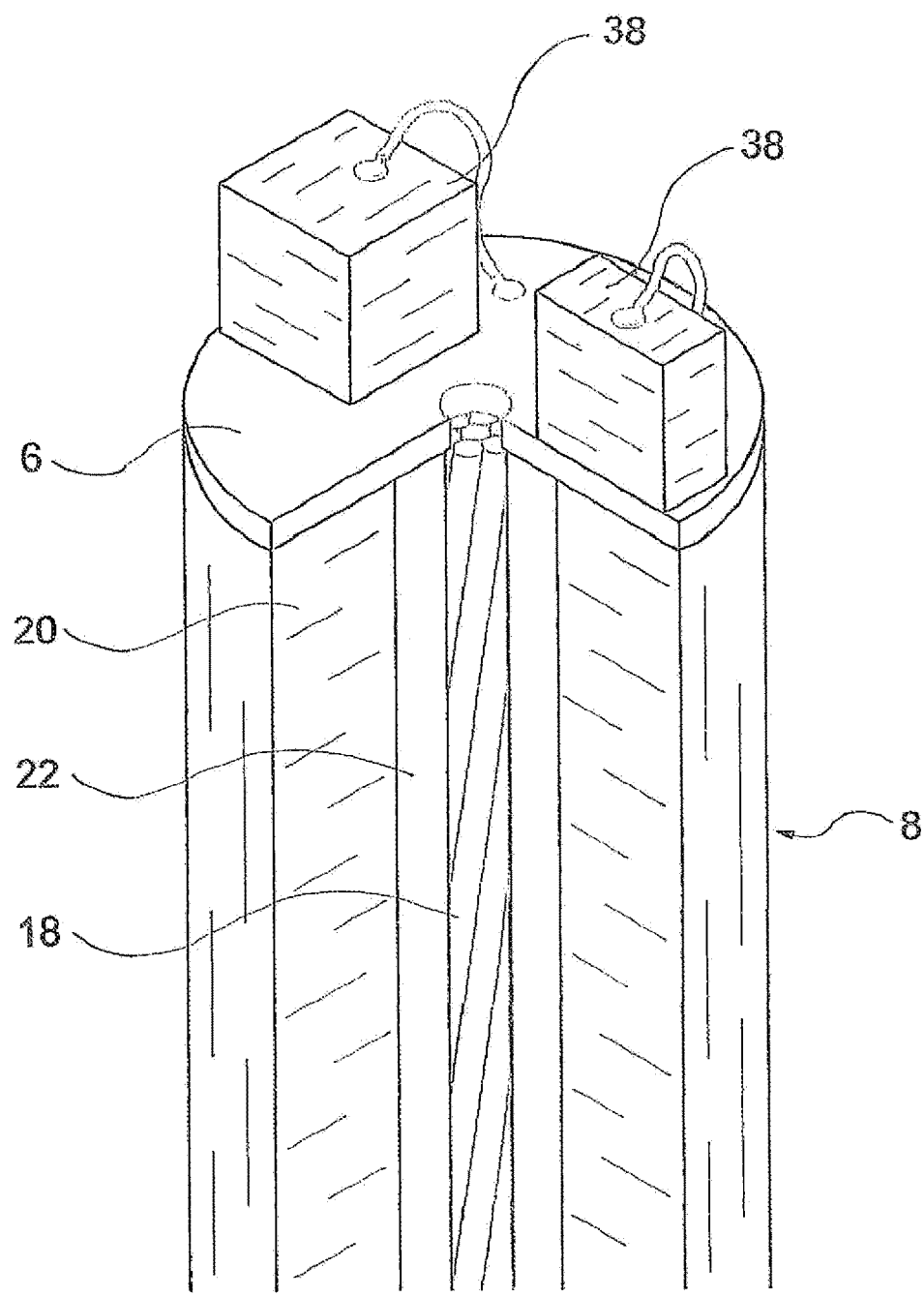
FIG. 11 is a partly sectioned view of a first example of the integration of two LEDs onto a connection lead.
Figure 12:
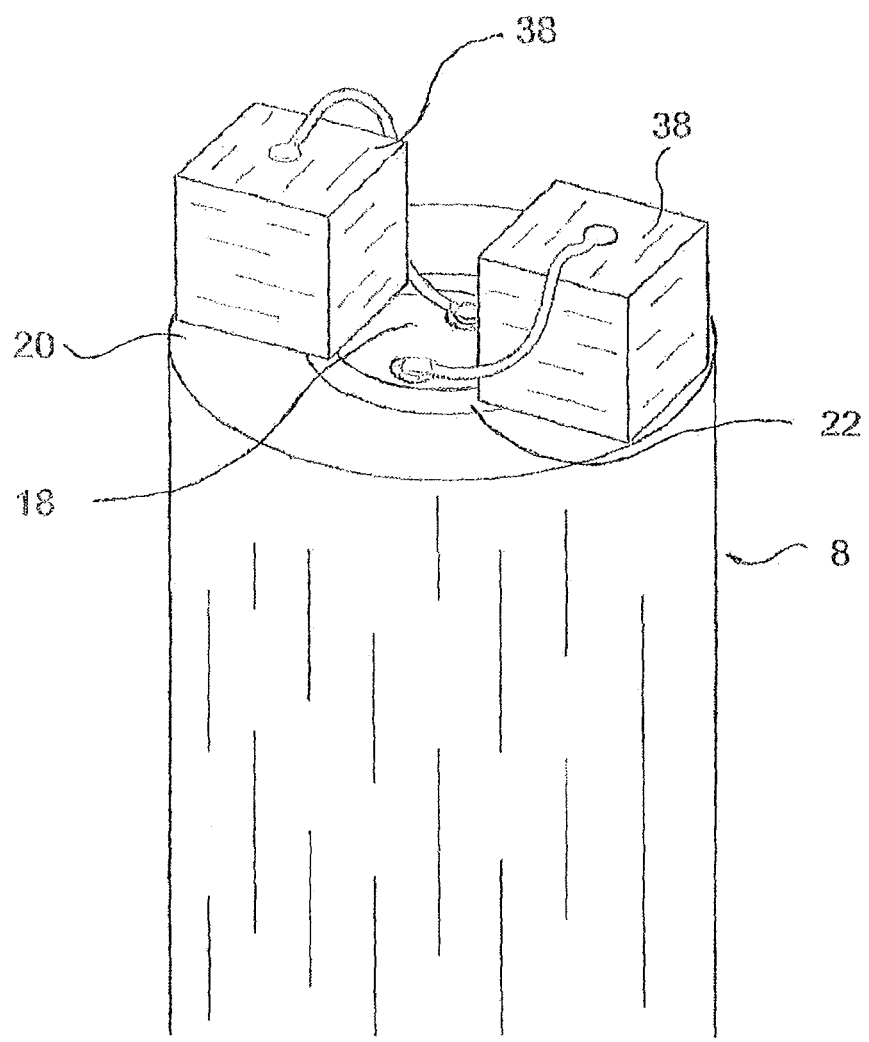
FIG. 12 is a perspective view of a second example of the integration of two LEDs onto a connection lead.
Figure 13:
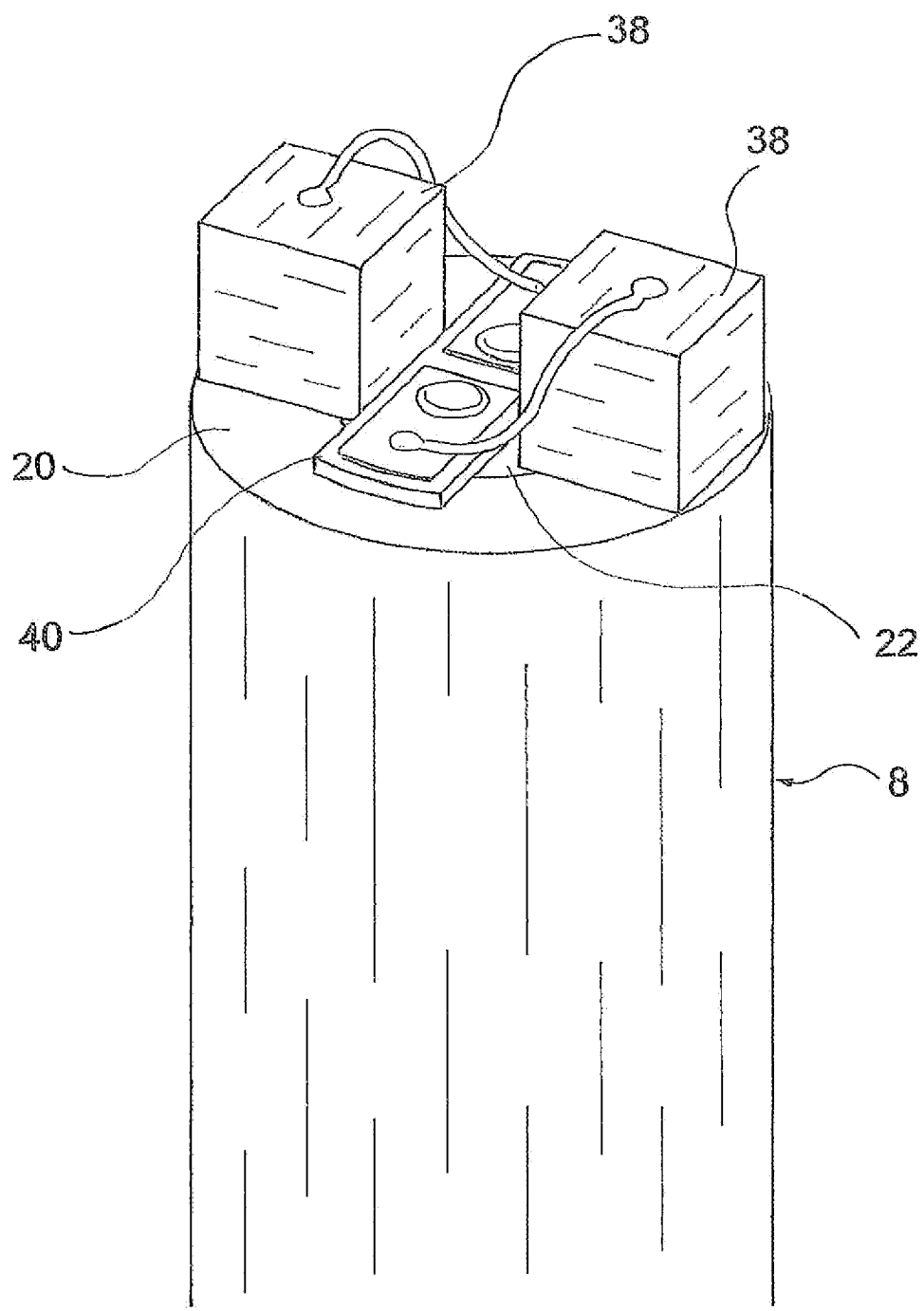
FIG. 13 is a perspective view of a third example of the integration of two LEDs onto a connection lead.

FIGS. 11 to 13 show three examples of the connection of LEDs 38, which form LED units 2, to a connection lead 8. The connection lead 8, in the form of a coaxial cable which is shown in FIG. 11, as previously described, has an inner and an outer conductor 18 and 20 with an insulation layer 22 lying therebetween. The distal end of the connection lead 8 abuts onto a connection plate 6 in a surfaced manner, so that here a highly thermally conductive, large-surfaced connection is created between the end of the connection lead 8 and the connection plate 6. For example, a thermally conductive bonding or soldering connection may be provided. With regard to the connection plate 6, if it is a circuit board, this is then designed in a very thin manner in the context of a low thermal resistance and a very good heat transfer in the longitudinal direction X. It may be provided with peripheral contacts, through-contacts or routings for a further reduction of the thermal resistance. Two LEDs 38, which form the LED unit 2, are attached on the connection plate 6 in an electrically conductive and heat-conducting manner. Thus here too, a highly thermally conductive connection is created between the LED 38 and the connection plate 6 in a suitable manner, so that the waste heat of the LED 38 is transmitted via the connection plate 6 onto the metallic conductors 18 and 20 of the connection lead 8 and may be led away from this in a proximal direction.

FIG. 12 shows an embodiment wherein the LEDs 38 forming the LED unit 2 are applied onto the end of the connection lead 8 in a direct manner. With the embodiment according to FIG. 12, two inner conductors 18 are provided, which are arranged insulated to one another within an insulation layer 22. In this manner, the two LEDs 38 may be supplied with energy independently of one another. Thus, the LEDs 38 may be activated differently within a single illumination module 38. With this, it is possible for example for the LEDs 38 to have different functions and to be able to apply these in a manner which is directed to the application (e.g., white light illumination with a white LED on the one hand and on the other hand fluorescence excitation with a blue LED). The LEDs 38 are arranged such that they bear directly on the end of the outer conductor 20 in a large surfaced manner, the conductor serving for leading away the heat. For this, a highly thermally conductive connection between the LEDs 38 and the outer conductor 20 is provided, for example by soldering or bonding. The inner conductors 18 are bonded, for example with gold wires, onto the respective connection surface of the LEDs 38.

The embodiment according to FIG. 13 corresponds to the embodiment according to FIG. 12, wherein a circuit board 40 is further arranged between the LEDs 38, which serves for the electrical contacting of the two LEDs 38 to the two inner conductors 18 (see FIG. 12).

The LED illumination modules according to the invention may be realized in a different shape. Then, one may apply suitable LED illumination modules according to the demands (light quantity, wavelength) and the geometric conditions in the endoscope.

Figure 14A:
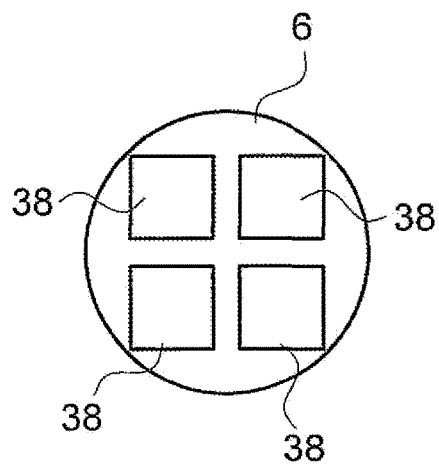
FIGS. 14*a*, 14*b* and 14*c* are respectively a distal-end plan view, a lateral view, and a perspective view of an embodiment with the integration of four LEDs onto a connection lead.
Figure 14B:
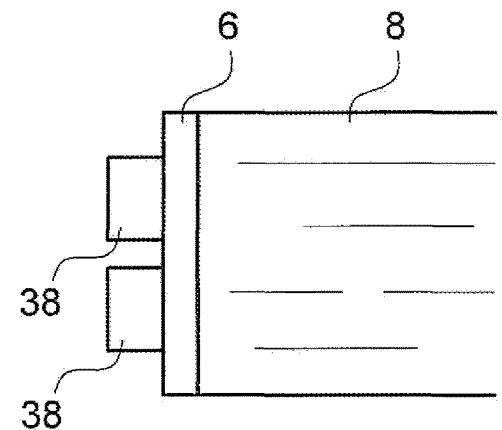
Figure 14C:
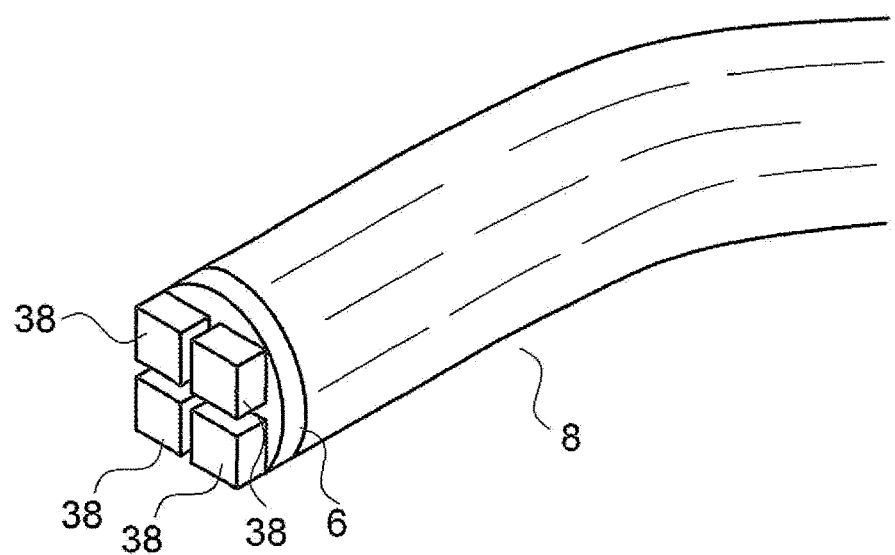

FIGS. 14a to 14c show a further embodiment which essentially corresponds to the embodiment according to FIG. 11, with the difference that four LEDs 38 are arranged on the connection plate 6. This LED illumination module is accordingly a light-intensive illumination module, which despite this has a comparatively low space requirement.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscopic instrument comprising a shank, at least one instrument channel or free channel opening to a distal end of the shank, at least one image sensor, at least one LED illumination module having at least one LED (38) arranged at a distal end of the instrument, and an electrical connection lead (8) attached to the at least one LED, wherein the connection lead (8) comprises a coaxial cable which extends from the distal end to a proximal end of the instrument and is designed for leading away waste heat produced by the LED (38), wherein a portion of the waste heat is dissipated from a periphery of the connection lead (8) to the shank, and from the shank to outer surroundings of the shank, the coaxial cable having at least one outer electrical conductor (20) surrounding at least one inner electrical conductor (18), and wherein at least one of the inner and outer electrical conductors (18, 20) is directly connected to the LED (38) in a heat-conducting manner.

2. The endoscopic instrument according to claim 1, wherein the connection lead (8) has the at least one inner and at least one outer electrical conductors (18, 20) connected to the LED (38) in a heat-conducting manner.

3. The endoscopic instrument according to claim 1, wherein at least one of the inner and outer electrical conductors (18, 20) of the connection lead (8) has a larger cross-sectional area than is necessary for electrical power transmission to the LED (38).

4. The endoscopic instrument according to claim 3, wherein the cross-sectional area is at least three times larger than is necessary for the electrical power transmission to the LED (38).

5. The endoscopic instrument according to claim 1, wherein at least one of the inner and outer electrical conductors (18, 20) of the connection lead (8) is connected to the LED (38) in a heat-conducting manner with a maximum of its cross-sectional area.

6. The endoscopic instrument according to claim 1, wherein the electrical connection lead (8) is connected in a heat-conducting manner to the LED (38) at a rear-side surface of the LED.

7. The endoscopic instrument according to claim 2, wherein at least the at least one outer conductor (20) of the electrical conductors of the connection lead (8) is connected to the LED (38) in a heat-conducting manner.

8. The endoscopic instrument according to claim 7, wherein the outer conductor (20) of the coaxial cable has a greater thickness in a radial direction of the coaxial cable than an insulation layer (22) situated between an inner conductor (18) and the outer conductor (20).

9. The endoscopic instrument according to claim 7, wherein the inner conductor (18) of the coaxial cable has a minimized cross-sectional area whose size is adapted to an electrical power to be transmitted.

10. The endoscopic instrument according to claim 7, wherein the outer conductor (20) of the coaxial cable has no electrical insulation at its outer periphery.

11. The endoscopic instrument according to claim 1, wherein the LED (38) is surrounded at least peripherally by elements (4, 36) having a lower thermal conductivity than a thermal conductivity of the electrical connection lead (8).

12. The endoscopic instrument according to claim 1, wherein the LED (38) is surrounded at least at a front end by elements (4, 36) having a lower thermal conductivity than a thermal conductivity of the electrical connection lead (8).

13. The endoscopic instrument according to claim 1, wherein the connection lead (8) is flexible.

14. The endoscopic instrument according to claim 2, wherein at least one of the inner and outer conductors of the connection lead comprises several individual conductors.

15. The endoscopic instrument according to claim 14, wherein the several individual conductors comprise a multitude of strands.

16. The endoscopic instrument according to claim 1, wherein the LED illumination module is designed to be exchangeable in the endoscopic instrument.

* * * * *